(12) United States Patent
Fournier et al.

(10) Patent No.: US 10,183,123 B2
(45) Date of Patent: Jan. 22, 2019

(54) NEEDLE PROTECTION DEVICE

(71) Applicant: APTAR STELMI SAS, Villepinte (FR)

(72) Inventors: Arnaud Fournier, Paris (FR); Ghislain Fournier, La Rochelle (FR); Mickaël Swal, Chauconin Neufmontiers (FR)

(73) Assignee: APTAR STELMI SAS, Villepinte (FR)

( * ) Notice: Subject to any disclaimer, the term of this patent is extended or adjusted under 35 U.S.C. 154(b) by 161 days.

(21) Appl. No.: 14/770,266

(22) PCT Filed: Feb. 25, 2014

(86) PCT No.: PCT/FR2014/050389
§ 371 (c)(1),
(2) Date: Aug. 25, 2015

(87) PCT Pub. No.: WO2014/131979
PCT Pub. Date: Sep. 4, 2014

(65) Prior Publication Data
US 2016/0001013 A1 Jan. 7, 2016

(30) Foreign Application Priority Data
Mar. 1, 2013 (FR) ..................... 13 51841

(51) Int. Cl.
*A61M 5/32* (2006.01)
*A61M 5/31* (2006.01)
(52) U.S. Cl.
CPC ........ *A61M 5/3204* (2013.01); *A61M 5/3202* (2013.01); *A61M 2005/3109* (2013.01); *A61M 2005/3118* (2013.01)
(58) Field of Classification Search
CPC .. A61M 2005/3109; A61M 2005/3118; A61M 5/3202; A61M 5/3204
See application file for complete search history.

(56) References Cited

U.S. PATENT DOCUMENTS 3,270,743 A * 9/1966 Gingras .............. A61M 5/3202
206/210
4,986,818 A * 1/1991 Imbert ................ A61M 5/3202
604/192

(Continued)

FOREIGN PATENT DOCUMENTS

EP    1 208 861 A1    5/2002
EP    1 466 638 A2    10/2004

(Continued)

OTHER PUBLICATIONS

International Search Report for PCT/FR2014/050389 dated Jun. 30, 2014 [PCT/ISA/210].

(Continued)

*Primary Examiner* — Quynh-Nhu H. Vu
(74) *Attorney, Agent, or Firm* — Sughrue Mion, PLLC

(57) ABSTRACT

Injection device of fluid product (100) comprising a syringe body (101) and a needle (110) fixed in an axial end projection (102) of the syringe body, said end projection (102) comprising an axial end surface (103), said injection device comprising a needle protection device (200), said protection device being, in a storage position, fixed on said injection device, said protection device being removable from said injection device, said protection device comprising an inner body (210) made of substantially supple and/or deformable material and an outer body (220) made of substantially rigid material, said inner body (210), in a storage position, sealingly closing the distribution orifice (111) of said needle (110) and sealingly cooperating with said injection device (100), and said outer body (220) comprising a fixing part (228) which, in a storage position, cooperates with a shoulder (104) of said injection device (100) for fixing said protection device (200) on said injection device (100), said inner body (210) comprising a proximal axial end edge (213) adapted, in a storage position, to sealingly cooperate (Continued)

Figure 3:
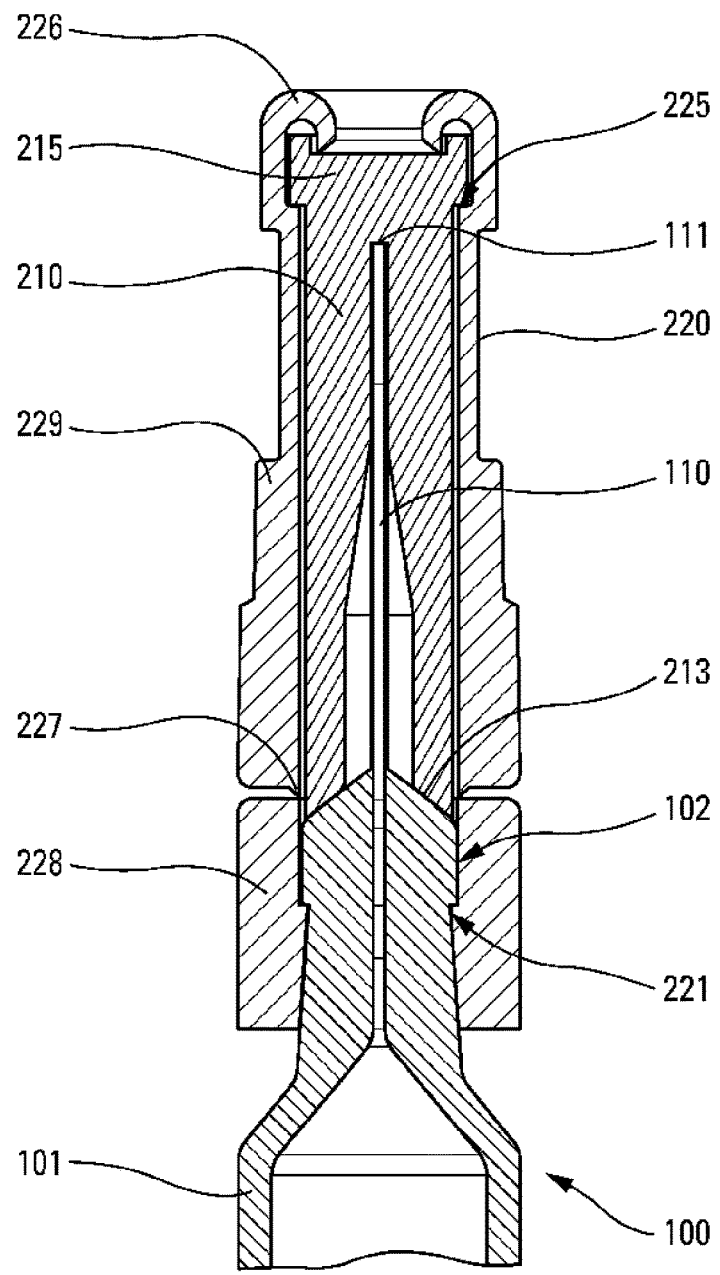

with the syringe body (101) only with said axial end surface (103), said inner body (210) being made of material having the following properties: a hardness greater than 55 Shore A, in particular greater than 60 Shore A, an elasticity greater than 8 MPa, in particular greater than 10 MPa, a compression set less than 30%, in particular less than 25%, a density greater than 1, in particular greater than 1.3.

16 Claims, 2 Drawing Sheets

(56) References Cited

U.S. PATENT DOCUMENTS

| | | | | |
|---|---|---|---|---|
| 5,084,027 | A | | 1/1992 | Bernard |
| 5,085,647 | A | * | 2/1992 | Henderson .......... A61M 5/3213 604/192 |
| 5,540,666 | A | * | 7/1996 | Barta .................. A61M 5/3202 604/110 |
| 5,746,733 | A | * | 5/1998 | Capaccio ............. A61J 1/2096 141/329 |
| 6,551,286 | B1 | * | 4/2003 | Claessens ........... A61M 5/3202 128/919 |
| 2002/0002354 | A1 | * | 1/2002 | Vetter ................. A61M 5/3202 604/272 |
| 2002/0062108 | A1 | * | 5/2002 | Courteix ............. A61M 5/3202 604/198 |
| 2008/0269690 | A1 | * | 10/2008 | Felix-Faure ........ A61M 5/3202 604/192 |
| 2009/0143746 | A1 | | 6/2009 | Mudd et al. |
| 2009/0187153 | A1 | | 7/2009 | West et al. |
| 2009/0198196 | A1 | | 8/2009 | West et al. |
| 2010/0198163 | A1 | * | 8/2010 | Bonnet ............... A61M 5/3202 604/192 |
| 2012/0330243 | A1 | * | 12/2012 | Liversidge .......... A61M 5/3213 604/198 |
| 2013/0012886 | A1 | * | 1/2013 | Kawachi ............. A61M 5/3202 604/192 |
| 2013/0030365 | A1 | * | 1/2013 | Liversidge .......... A61M 5/3202 604/111 |
| 2014/0050514 | A1 | * | 2/2014 | Uehara ................ A45D 40/262 401/143 |

FOREIGN PATENT DOCUMENTS

| | | |
|---|---|---|
| EP | 1 795 220 A1 | 6/2007 |
| FR | 2 777 787 A1 | 10/1999 |
| WO | 02/074367 A2 | 9/2002 |
| WO | 2011/131996 A1 | 10/2011 |

OTHER PUBLICATIONS

International Preliminary Examination Report for PCT/FR2014/050389 dated Jun. 30, 2014 [PCT/IPEA/409].

International Preliminary Report on Patentability dated Sep. 3, 2015 from the International Searching Authority in counterpart application No. PCT/FR2014/050389.

* cited by examiner

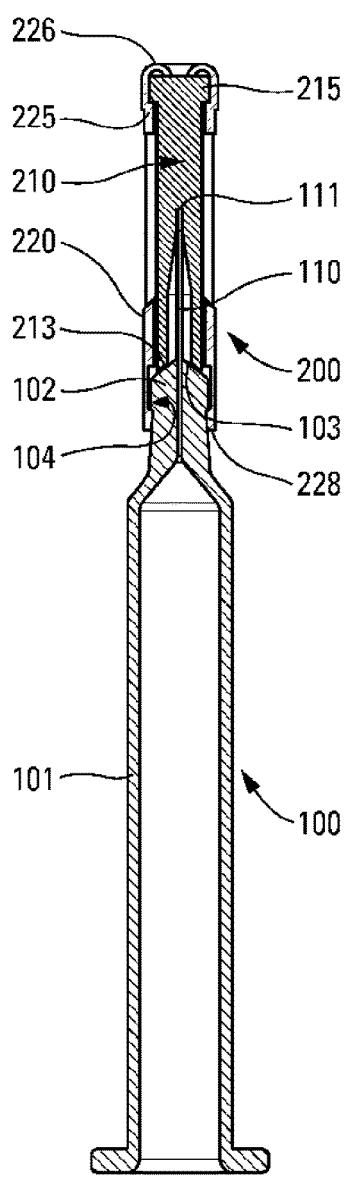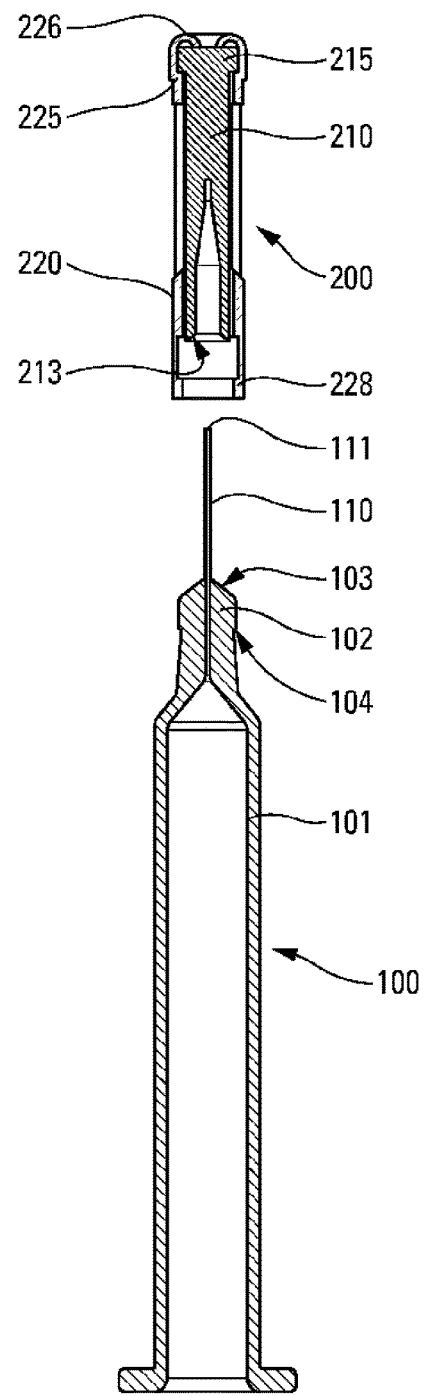
Fig. 1
Fig. 2

NEEDLE PROTECTION DEVICE

CROSS REFERENCE TO RELATED APPLICATIONS

This application is a National Stage of International Application No. PCT/FR2014/050389 filed Feb. 25, 2014, claiming priority based on French Patent Application No. 1351841 filed Mar. 1, 2013, the contents of all of which are incorporated herein by reference in their entirety.

The present invention relates to an injection device comprising a removable needle protection device.

Needle protection devices, also called needle protectors, are well known. There are different types of them, including rigid needle protectors, comprising an inner body made of supple material and an outer body made of rigid material. The inner body ensures sealing both with the orifice of the needle and with the injection device, in general the syringe body, whereas the outer body serves to fix and maintain the needle protector on the injection device until it is used. Documents EP 1 208 861 and FR 2 777 787 in particular describe needle protection devices of this type.

These devices can have disadvantages. Therefore, due in particular to manufacturing tolerances, in particular glass syringes, it can be difficult in some cases to guarantee sealing in a storage position between the deformable inner body of the needle protector and the injection device, in this case the glass syringe body. Also, it is generally not possible to prevent unwanted or accidental withdrawal of the needle protector before use of the associated injection device, which involves the risk of needle contamination. Also, manufacture and assembly of the needle protector, and in particular of the outer body on the inner body, can be complex and therefore costly.

Document WO 2011/131996 describes a device of the prior art with a needle protector made of elastomer.

The aim of the present invention is to provide an injection device which does not replicate the above disadvantages.

The aim of the present invention is therefore to provide an injection device ensuring sealing before use.

Another aim of the present invention is to provide an injection device which is simple and easy to manufacture and assemble, and reliable in use.

The aim of the present invention therefore is an injection device of fluid product comprising a syringe body and a needle fixed in an axial end projection of the syringe body, said end projection comprising an axial end surface, said injection device comprising a needle protection device, said protection device being, in a storage position, fixed on said injection device, said protection device being removable from said injection device, said protection device comprising an inner body made of substantially supple and/or deformable material and an outer body made of substantially rigid material, said inner body, in a storage position, sealingly closing the distribution orifice of said needle and sealingly cooperating with said injection device, and said outer body comprising a fixing part which, in a storage position, cooperates with a shoulder of said injection device to fix said protection device on said injection device, said inner body comprising a proximal axial end edge adapted, in a storage position, to sealingly cooperate with the syringe body only with said axial end surface, said inner body being made of material having the following properties: a hardness greater than 55 Shore A, in particular greater than 60 Shore A, an elasticity greater than 8 MPa, in particular greater than 10 MPa, a compression set less than 30%, in particular less than 25%, a density greater than 1, in particular greater than 1.3.

Advantageously, said inner body is made of rubber.

Advantageously, said body comprises a radial projection and said outer body comprises a radial shoulder and a radial end edge defining an upper axial opening, said inner body being inserted into said outer body through said upper axial opening, with said radial projection stopped on said radial shoulder, said axial end edge of said outer body being folded back on said inner body to fix said inner body in said outer body.

Advantageously, said fixing part is clipped on to said shoulder.

Advantageously, said outer body comprises a protection part fixed to said inner body, said protection part connected to said fixing part by at least one breakable material bridge, said at least one breakable material bridge being broken to withdraw said protection part and said inner body from said injection device.

Advantageously, the force necessary to withdraw said fixing part from said injection device is greater than the force necessary to break said at least one breakable material bridge.

Advantageously, folding back is carried out under heat, typically between 100° C. and 200° C.

Advantageously, said inner body, when subjected to high temperatures, for example steam sterilisation at around 120° C., has dimensional modifications less than 2%, advantageously less than 1%, preferably less than 0.5%.

Advantageously, said injection device is a syringe.

Advantageously, said injection device is an auto-injector.

These characteristics and advantages and others of the present invention will emerge more clearly from the following detailed description, given in reference to the appended drawings given by way of non-limiting examples, in which:

FIGS. 1 and 2 are schematic views in transversal section of a needle protection device according to a first advantageous variant embodiment, respectively in a storage position on an injection device and in withdrawn position, and FIG. 3 is a schematic view in transversal section of an advantageous variant embodiment, in storage position.

The present invention will be described in reference to several variant embodiments of a needle protection device for an injection device. It is nevertheless understood that the present invention is not limited by the embodiments illustrated in the drawings.

In reference to FIGS. 1 and 2, these illustrate an injection device which in this example is a syringe 100 provided with a syringe body 101 and a needle 110 comprising a distribution orifice 111. The axial end part of the syringe body where is fixed the needle 110 comprises an axial end projection 102, generally called bowl of the syringe, defined between the axial end surface 103 of the syringe body and a radial projection 104 provided to receive and fix a needle protection device 200, to be described hereinbelow. The needle typically has a length of 12.7 mm (½ inch), 15.9 mm (⅝ inch) or 25.4 mm (1 inch). Other dimensions are also possible.

A needle protection device 200 is provided to protect and maintain sealed said needle until the injection device is used. The needle protection device 200 is fixed on said injection device 100 in a storage position, and it is removable, that is, it can be removed from said injection device when said injection device is being used. The needle protection device 200 comprises an inner body 210 and an outer body 220.

The inner body 210 is made of substantially supple or deformable material. The inner body 210 comprises a full part which, in a storage position of the needle protection device, receives the distribution orifice 111 of the needle 110. The axial end of the needle 110 is therefore embedded in said inner body 210 in said storage position. The inner body 210 also comprises a radial projection 215 formed at the distal axial end of said inner body relative to said injection device. On the other side, at the other axial end, the inner body 210 forms a hollow sleeve and comprises a proximal axial end edge 213 relative to the injection device whereof the form is complementary to the axial end surface 103 of the bowl of the syringe 102.

The outer body 220 is made, preferably single piece, of substantially rigid material, such as for example polypropylene (PP), polystyrene (PS), polyoxymethylene (POM) or polybutylene terephthalate (PBT). Other materials are also possible. The outer body 220 comprises a fixing part 228 which is adapted to cooperate with the syringe body 101, in particular with the bowl of the syringe 102, and more particularly with the radial shoulder 104, to fix, in particular by clipping, said needle protection device 200 onto said injection device 100. The outer body 220 comprises on the other side, namely on the distal side relative to the injection device, a radial shoulder 225 and an axial end edge 226 which defines an upper axial opening. Said axial end edge can be folded back inwardly, as will be explained later.

The needle protection device 200 is advantageously made by molding inner body 210 and outer body 220, then assembly of the inner body in the outer body. Preferably, the inner body is inserted into the outer body via the upper opening until the radial projection 215 of the inner body 210 comes to bear on the radial shoulder 225 of the outer body 220. The axial end edge 226 of the outer body 220 is then folded back for fixedly holding the inner body 210 in the outer body 220. This folding back can be done before or after assembly of the needle protection device 200 on the injection device 100. Folding back of the axial end edge 226 is preferably done under heat, typically between 100° C. and 200° C. as a function of the material of the outer body.

In the storage position, sealing with the needle 110 is achieved by embedding the distribution orifice 111 of the needle 110 in the supple or deformable material of the inner body 210.

According to the invention, the sealing with the injection device is achieved exclusively by contact between the axial end edge 213 of the inner body 210 and the axial end surface 103 of the bowl of the syringe 102. Said inner body 210 is made of material having the following properties: a hardness greater than 55 Shore A, advantageously greater than 60 Shore A, an elasticity greater than 8 MPa, advantageously greater than 10 MPa, a compression set less than 30%, advantageously less than 25%, a density greater than 1, advantageously greater than 1.3. More particularly, said inner body is made of rubber.

To obtain good sealing, it is necessary to compress the inner body 210 on the bowl 102 of the syringe. Ensuring sealing at this level is critical due to the small available surface: around 12 mm², compared to protection devices which achieve sealing at least in part on the lateral side of the bowl of the syringe, and which have at least 40 mm².

Rubber proves much better than TPE (thermoplastic elastomer) for making the inner body according to the invention. In fact, rubber transmits greater force at the level of the sealing surface as it combines greater hardness and elasticity as compared to TPE.

For rubber, hardness is greater than 55 Shore A, generally even greater than 60 Shore A and elasticity is greater than 8 MPa, generally even greater than 10 MPa. This must be compared to degrees of hardness of TPE not exceeding 55 Shore A and degrees of oscillating elasticity between 4 and 12 MPa. It should be noted that for TPE, never is considerable hardness associated with considerable elasticity. In fact, as hardness of the TPE is also a function of the elasticity of the latter, the greater the hardness the less its elasticity. This is not the case for rubbers.

Over time rubber could guarantee determined homogeneous compression since its DRC (compression set) is less than that of TPE. Rubber typically has DRC less than 30%, generally even less than 25%, compared to TPE having DRC which can reach values greater than 40%.

Rubber also has dimensional stability which lets it undergo different treatment, such as steam sterilisation. This shows up as a notable difference to TPE, which can shrink, that is, a dimensional decrease. In fact, at high temperature, for example around 120° C. during steam sterilisation, TPE can shrink as much as 3%. This shows up as reduction in its total length and loss of tightness. Rubber does not have this dimensional variation, in particular during steam sterilisation. In particular, rubber, when subjected to high temperatures, for example steam sterilisation at around 120° C., has dimensional modifications less than 2%, advantageously less than 1%, preferably less than 0.5%.

The following materials can in particular be used within the scope of the present invention: mixtures of rubber elastomers including in their composition at least one of the following rubber elastomers: styrene-butadiene (SBR) copolymers, polybutadienes (BR), natural polyisoprenes (IR) or synthesis, copolymers based on isobutylene and isoprene, halogenated or not (IIR, CIIR, BIIR), copolymers or terpolymers based on ethylene and propylene (EPM, EPDM) and butadienes-acrylonitrile (NBR) copolymers.

These mixes of rubber are composed of polymers of different types, and they can comprise mineral charges, of carbon black type, silicas, kaolins, talc, etc.

These mixes of rubber can also comprise different types of vulcanisation agents, plastifiers, dyes or protection agents.

The following table compares the properties of rubber based on polyisoprene with different TPE, respectively based on SEBS (polystyrene-b-poly(ethylene-butylene)-b-polystyrene) and EPDM (ethylene-propylene-diene monomer).

|  |  | Poly-isopre | SEBS-based TPE | EPDM-based TPE | Method |
| --- | --- | --- | --- | --- | --- |
| Density |  | — | 1.35 | 0.92 | 0.93 ASTM D 792 |
| Hardness | Shore A | 61 | 51 | 55 | ASTM D 2240 |
| Steam | g/m² · j | 4.98 | 2.88 | 3.28 | ASTM F 1249 water |
| Elasticity | MPa | 11.1 | 12 | 4.6 | ASTM D 412 |
| Elongation | % | 500 | 800 | 480 | ASTM D 412 |
| DRC | % | 23 | 42 | 27 | ASTM D 395 (B- 22 h- 70° C. |

FIG. 3 shows an advantageous variant embodiment incorporating proof of initial usage.

In this variant, the outer body 220 comprises a protection part 229 which is connected to the fixing part 228 by at least one breakable material bridge 227. So, the outer body 220 is made of a single piece, and during withdrawal of the needle protection device, said at least one breakable material bridge 227 is broken, which forms proof of initial usage. For the needle protection device to be withdrawn, the breakable material bridge(s) has/have to be broken, and once broken it is no longer possible to return it to the initial state. The user who sees intact material bridges therefore knows that the needle protection device has not been removed. If on the contrary the material bridges are broken, he knows that there is the risk of loss of sealing and therefore contamination. Of course, the force necessary to disassemble the fixing part 228 of the injection device 100 must be greater than the force necessary to break the material bridge or bridges. Therefore, it is ensured that it is always the material bridges which will break first, and it will not be possible to remove the needle protection device without breaking said material bridges.

The fixing part 228 is fixed on the injection device, in particular clipped on the bowl of the syringe, as described previously. The protection part 229 is fixed to said inner body 210, in particular by wedging of the radial projection 215 of the inner body 210 between the radial shoulder 225 and the axial end edge folded back 226.

In the variant embodiment of FIG. 3, the material bridges 227 are broken by axially pulling on the protection part 229. When there is sufficient force, the material bridges 227 break, and the protection part together with the inner body 210 can be withdrawn from the injection device 100, while the fixing part 228 remains fixed to the bowl of the syringe.

Of course, the invention is not limited to the embodiments illustrated in the drawings, and by contrast the scope of the invention is defined by the appended claims.

The invention claimed is:

1. An injection device of fluid product comprising a syringe body and a needle fixed in an axial end projection of the syringe body, said end projection comprising an axial end surface and a radial shoulder, said injection device comprising a needle protection device, said protection device being, in a storage position, fixed to said syringe body, said protection device being removable from said syringe body, said protection device comprising an inner body made of substantially supple and/or deformable material and an outer body made of substantially rigid material and both said inner body and said outer body are secured to each other to form an integral construction so that the integral construction is removable from the syringe body while retaining the integral construction intact, and wherein said inner body, in a storage position, sealingly closing the distribution orifice of said needle and sealingly cooperating with said syringe body, and said outer body comprising a fixing part which, in a storage position, cooperates with said radial shoulder of said end projection to fix said protection device onto said syringe body, wherein said inner body comprises a proximal axial end edge adapted, in a storage position, to sealingly cooperate with the syringe body only with said axial end surface, said inner body being made of material having the following properties: a hardness greater than 55 Shore A, an elasticity greater than 8 MPa, a compression set less than 30%, a density greater than 1.

2. The device according to claim 1, wherein said inner body is made of rubber.

3. The device according to claim 1, wherein said inner body comprises a radial projection and said outer body comprises a radial shoulder and an axial end edge defining an upper axial opening, said inner body being inserted into said outer body through said upper axial opening, with said radial projection stopped on said radial shoulder, said axial end edge of said outer body being folded back on said inner body to fix said inner body in said outer body.

4. The device according to claim 3, wherein folding back of the axial end edge of the outer body is carried out under heat between 100° C. and 200° C.

5. The device according to claim 1, wherein said fixing part is clipped on said shoulder.

6. The device according to claim 5, wherein said outer body comprises a protection part fixed to said inner body, said protection part connected to said fixing part by at least one breakable material bridge, said at least one breakable material bridge being broken to remove said protection part and said inner body from said syringe body.

7. The device according to claim 6, wherein a force necessary to remove said fixing part is greater than the force necessary to break said at least one breakable material bridge.

8. The device according to claim 1, wherein said inner body, when subjected to high temperatures, steam sterilisation has dimensional modifications less than 2%.

9. The device according to claim 1, wherein said injection device is a syringe.

10. The device according to claim 1, wherein the inner body is made of material having a hardness greater than 60 Shore A.

11. The device according to claim 1, wherein the inner body is made of material having an elasticity greater than 10 MPa.

12. The device according to claim 1, wherein the inner body is made of material having a compression set less than 25%.

13. The device according to claim 1, wherein the inner body is made of material having a density greater than 1.3.

14. The device according to claim 1, wherein the inner body is made of material having a hardness greater than 60 Shore A, an elasticity greater than 10 MPa, a compression set less than 25%, and a density greater than 1.3.

15. The device according to claim 1, wherein said inner body, when subjected to high temperatures, steam sterilisation at around 120° C. has dimensional modifications less than 1%.

16. The device according to claim 1, wherein said inner body, when subjected to high temperatures, steam sterilisation at around 120° C. has dimensional modifications less than 0.5%.

* * * * *